ization," Kansas City Star, 2014, https://kansascity.com/news/

(12) United States Patent
Shah

(10) Patent No.: US 11,291,631 B2
(45) Date of Patent: Apr. 5, 2022

(54) ORAL CANNABINOID FORMULATIONS

(71) Applicant: GW Research Limited, Cambridge (GB)

(72) Inventor: Harshit Shah, Cambridge (GB)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 16/314,569

(22) PCT Filed: Jun. 29, 2017

(86) PCT No.: PCT/GB2017/051914
§ 371 (c)(1),
(2) Date: Dec. 31, 2018

(87) PCT Pub. No.: WO2018/002637
PCT Pub. Date: Jan. 4, 2018

(65) Prior Publication Data
US 2019/0167583 A1    Jun. 6, 2019

(30) Foreign Application Priority Data

Jul. 1, 2016 (EP) ...................... 1611547

(51) Int. Cl.
| | |
|---|---|
| *A23L 27/30* | (2016.01) |
| *A61K 31/05* | (2006.01) |
| *A61K 9/08* | (2006.01) |
| *A61K 47/10* | (2017.01) |
| *A61K 47/14* | (2017.01) |
| *A61K 47/44* | (2017.01) |
| *A61K 9/00* | (2006.01) |
| *A61P 25/08* | (2006.01) |

(52) U.S. Cl.
CPC .............. *A61K 9/08* (2013.01); *A61K 9/0095* (2013.01); *A61K 31/05* (2013.01); *A61K 47/10* (2013.01); *A61K 47/14* (2013.01); *A61K 47/44* (2013.01); *A61P 25/08* (2018.01)

(58) Field of Classification Search
CPC .......... A61K 9/08; A61K 31/05; A61K 47/14; A61K 47/44; A61K 9/0095; A61K 47/10; A23L 27/30; A23L 27/84; A23L 27/86; A23V 2200/16
See application file for complete search history.

(56) References Cited

U.S. PATENT DOCUMENTS

| | | |
|---|---|---|
| 6,403,126 B1 | 6/2002 | Webster |
| 6,949,582 B1 | 9/2005 | Wallace |
| 8,293,786 B2 | 10/2012 | Stinchcomb |
| 8,673,368 B2 | 3/2014 | Guy et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,522,123 B2 | 12/2016 | Whalley et al. |
| 9,730,911 B2 | 8/2017 | Verzura et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 10,092,525 B2 | 10/2018 | Guy et al. |
| 10,111,840 B2 | 10/2018 | Guy et al. |
| 10,137,095 B2 | 11/2018 | Guy et al. |
| 2004/0049059 A1 | 3/2004 | Muller |
| 2004/0110828 A1 | 6/2004 | Chowdhury et al. |
| 2005/0042172 A1 | 2/2005 | Whittle |
| 2005/0266108 A1 | 12/2005 | Flockhart et al. |
| 2006/0039959 A1 | 2/2006 | Wessling |
| 2007/0060638 A1 | 3/2007 | Olmstead |
| 2007/0060639 A1* | 3/2007 | Wermeling .......... A61K 9/0043 514/454 |
| 2008/0119544 A1 | 5/2008 | Guy et al. |
| 2008/0188461 A1 | 8/2008 | Guan |
| 2009/0035368 A1 | 2/2009 | Moschwitzer |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |

(Continued)

FOREIGN PATENT DOCUMENTS

| | | |
|---|---|---|
| CA | 2737447 | 10/2012 |
| CA | 2859934 | 3/2016 |

(Continued)

OTHER PUBLICATIONS

[No Author Listed], "Missouri House passes cannabis extract legpolitics-govemment/article346747.html, 2 pages.
Cdc.gov [online], "2 to 20 years: Girls Stature-for-age and Weighfor-age percentiles," National Center for Health Statistics and National Center for Chronic Disease Prevention and Health Promotion, last modified Nov. 2000, <https://www.cdc.gov/growthcharts/data/set1clinical/cj411022.pdf>, 1 page.

(Continued)

*Primary Examiner* — Theodore R. Howell
(74) *Attorney, Agent, or Firm* — Cooley LLP

(57) ABSTRACT

The present invention relates to a cannabinoid containing oral solution. Preferably the oral solution comprises a cannabinoid, a lipid solvent, a sweetener and ethanol, characterised in that the sweetener is an ultrahigh potency sweetener.

20 Claims, No Drawings

(56) References Cited

U.S. PATENT DOCUMENTS

| | | |
|---|---|---|
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0231083 A1 | 9/2012 | Carley et al. |
| 2012/0270845 A1 | 10/2012 | Bannister et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0110828 A1 | 4/2014 | Otremba et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0342902 A1* | 12/2015 | Vangara .............. A61K 47/44 514/729 |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2016/0271252 A1 | 9/2016 | Vangara et al. |
| 2016/0367496 A1 | 12/2016 | Vangara et al. |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0224634 A1 | 8/2017 | Vangara et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0028489 A1 | 2/2018 | Vangara et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0083418 A1 | 3/2019 | Guy et al. |
| 2019/0175547 A1 | 6/2019 | Stott et al. |
| 2019/0314296 A1 | 10/2019 | Wright et al. |
| 2021/0330797 A1 | 10/2021 | Vangara et al. |

FOREIGN PATENT DOCUMENTS

| | | |
|---|---|---|
| CN | 101040855 | 9/2007 |
| CN | 103110582 | 5/2013 |
| CN | 104840967 A | 8/2015 |
| DE | 102012-105063 | 12/2013 |
| EP | 2448637 | 5/2012 |
| EP | 2 741 750 A1 | 6/2014 |
| GB | 2384707 | 8/2003 |
| GB | 2434097 | 7/2007 |
| GB | 2434312 | 7/2007 |
| GB | 2438682 A | 12/2007 |
| GB | 2450753 | 1/2009 |
| GB | 0911580.9 | 7/2009 |
| GB | 2456183 | 7/2009 |
| GB | 2471523 | 1/2011 |
| GB | 2478595 | 9/2011 |
| GB | 2479153 | 10/2011 |
| GB | 2471565 | 7/2012 |
| GB | 2478072 | 12/2012 |
| GB | 2478074 | 12/2012 |
| GB | 2492487 | 1/2013 |
| GB | 2487712 | 10/2015 |
| GB | 2531282 A | 4/2016 |
| JP | 2010-270110 A | 12/2010 |
| WO | WO 01/28590 A2 | 4/2001 |
| WO | WO 2002/064109 | 8/2002 |
| WO | WO 2003/099302 | 12/2003 |
| WO | WO 2004/016246 | 2/2004 |
| WO | WO 2004/016277 | 2/2004 |
| WO | WO 2006/054057 | 5/2006 |
| WO | WO 2006/133941 | 12/2006 |
| WO | WO 2007/032962 * | 3/2007 |
| WO | WO 2007/083098 | 7/2007 |
| WO | WO 2007/138322 | 12/2007 |
| WO | WO 2008/019146 | 2/2008 |
| WO | WO 2008/024490 A | 2/2008 |
| WO | WO 2008/094181 | 8/2008 |
| WO | WO 2008/129258 | 10/2008 |
| WO | WO 2008/144475 | 11/2008 |
| WO | WO 2008/021394 | 12/2008 |
| WO | WO 2008/146006 | 12/2008 |
| WO | WO 2009/007697 | 1/2009 |
| WO | WO 2009/007698 | 1/2009 |
| WO | WO 2009/020666 | 12/2009 |
| WO | WO 2010/012506 A1 | 2/2010 |
| WO | WO 2011/001169 | 1/2011 |
| WO | WO 2011/121351 | 10/2011 |
| WO | WO 2012/033478 | 3/2012 |
| WO | WO 2012/093255 | 7/2012 |
| WO | WO 2013/024373 A1 | 2/2013 |
| WO | WO 2013/032351 | 3/2013 |
| WO | WO 2014/146699 A1 | 9/2014 |
| WO | WO 2015/142501 | 9/2015 |
| WO | WO 2015/184127 | 12/2015 |
| WO | WO 2015/193667 | 12/2015 |
| WO | WO 2015/193668 | 12/2015 |
| WO | WO 2016/059405 * | 4/2016 |
| WO | WO 2016/084075 | 6/2016 |
| WO | WO 2016/118391 | 7/2016 |
| WO | WO 2016/147186 | 9/2016 |
| WO | WO 2016/022936 | 11/2016 |
| WO | WO 2016/199148 | 12/2016 |
| WO | WO 2017/168138 | 10/2017 |
| WO | WO 2018/002636 | 1/2018 |
| WO | WO 2018/002637 | 1/2018 |
| WO | WO 2018/035030 A1 | 2/2018 |
| WO | WO 2018/037203 | 3/2018 |
| WO | WO 2018/037203 A1 | 3/2018 |
| WO | WO 2019/082171 A1 | 5/2019 |
| WO | WO 2019/159174 A1 | 8/2019 |
| WO | WO 2020/240184 A1 | 12/2020 |

OTHER PUBLICATIONS

Chou, "Theoretical basis, experimental design, and computerized simulation of synergism and antagonism in drug combination studies," Pharmacol Rev., Sep. 2006, 58(3), 621-681.

Kuhn et al., "Potent activity of carfilzomib, a novel, irreversible inhibitor of the ubiquitin-proteasome pathway, against preclinical models of multiple myeloma," Blood, Nov. 2007, 110(9): 3281-3290.

Morelli et al., "The effects of cannabidiol and its synergism with bortezomib in multiple myeloma cell lines. A role for transient receptor potential Vanilloid type-2," Int J Cancer, Jun. 2014, 134(11): 2534-2546.

Nabissi et al., "Cannabinoids synergize with cafilzomib, reducing multiple myeloma cells viability and migration," Oncotarget, Oct. 2016, 7: 77553.

PCT International Preliminary Report on Patentability in International Appln. No. PCT/GB2017/052229, dated Feb. 26, 2019, 7 pages.

PCT International Search Report and Written Opinion in International Appln. No. PCT/GB2017/052229, dated Oct. 6, 2017, 10 pages.

(56) References Cited

OTHER PUBLICATIONS

Raab et al., "Multiple myeloma," Lancet, Jul. 2009, 374(9686): 324-339.
Velasco et al., "Anticancer mechanisms of cannabinoids," Curr Oncol, Mar. 2016, 23(2): S23-S32.
[No Author Listed] "Cannabidiol Therapy for Aicardi Syndrome" Aug. 2014, 4 pages.
[No Author Listed], Cover and Table of Contents, J Pharmacology and Exp Therapeutics, Feb. 2010, 332(2), 4 pages.
Alger, "Not Too Excited? Thank Your Endocannabinoids," Neuron., Aug. 2006, 51(4):393-395.
American Epilepsy Society, Three Studies Shed New Light on the Effectiveness of Cannabis in Epilepsy, Oct. 14, 2014, 2 pages.
Ames et al., "Anticonvulsant effect of cannabidiol," S. Afr Med. J., Jan. 1986, 69(1):14.
Arain et al., "Pregabalin in the Management of Partial Epilepsy," Neuropsychiatr Dis Treat., Aug. 2009, 5:407-413.
Arslan and Tirnaksiz, "Self-emulsifying Drug Delivery Systems," FABAD J Pharm Sci, 2013,38(1):55-64.
Arzimanoglou et al., "All children who experience epileptic falls do not necessarily have Lennox-Gastaut syndrome . . . but many do," Epileptic Discord, 2011, 13:S3-S13.
AU Third Party Observations for Application No. AU2012314129, dated Mar. 19, 2015, 51 pages.
Avoli et al., "Cellular and molecular mechanisms of epilepsy in the human brain," Prog Neurobiol., 2005, 77(3):166-200.
Bakhsm, "Key Attributes of TKDL," Miftaah-al-Khazaain, 1930, 607-608 (with English translation).
Bancaud et al., "Proposal for Revised Clinical and Electroencephalographic Classification of Epileptic Seizures," Epilepsia, Aug. 1981, 22(4):489-501.
Banerjee et al., "Case Report: Aicardi syndrome: A report of five Indian cases," Neurology India, Mar. 2006, 54(1): 91-93.
Barker-Haliski et al, "How Clinical Development Can, and Should. Inform Translational Science," Neuron, Nov. 2014, 84: 582-593.
Benowitz et al., "Metabolic and Psychophysiologic studies of cannabidiol hexobarbital interaction," Clin Pharmacol Ther., 1980, 28(1):115-120.
Bertram, "The Relevance of Kindling for Human Epilepsy," Epilepsia, Apr. 2007, 48(Suppl. 2):65-74.
Bhatt et al., "Indigenous Plants in Traditional Healthcare System in Kedarnath Valley of Western Himalaya," Indian J Tradit Knowl., Apr. 2008, 7(2):300-310.
Bhattacharyya et al., "Modulation of mediotemporal and ventrostriatal function in humans by Delta9-tetrahydrocannabinol: a neural basis for the effects of Cannabis sativa on learning and psychosis," Arch Gen Psychiatry., 2009, 66:442-451.
BipolarHealthGroup.org [online], "Charlotte's Web Hemp Remedy," Bipolar Health Group, available on or before Sep. 6, 2017 , retrieved on May 21, 2018, URL <http:/bipolarhealthgroup.org/index.php/charlottes-web-hemp-remedy/>, 6 pages.
Booth et al., "Legalization's opening of medical pot research is dream and nightmare," Denver Post, Dec. 14, 2013, retrieved on Feb. 8, 2017, URL <https://www.denverpost.com/2013/12/14/legalizations-opening-of-medical-pot-research-is-dream-and-nightmare/>, 6 pages.
Bostanci et al., "The effects of octanol on penicillin induced epileptiform activity in rats: An in vivo study," Epilepsy Res., Jul. 27, 2006, 71(2-3):188-194.
Braida et al., "Post-ischemic treatment with cannabidiol prevents electroencephalographic flattening, hyper locomotion and neuronal injmy in gerbils" Neuroscience Letters., 2003, 346:61-64.
Brust et al., "Marijuana use and the risk of new onset seizures," Trans Am Clin Climatol Assoc., 1992, 103:176-181.
Carlini et al., "Hypnotic and Antiepileptic Effects of Cannabidiol," J Clin Pharmacol., Aug.-Sep. 1981, 21(8-9 Suppl):417S-427S.
Castel-Branco et al., "The Maximal Electroshock Seizure (MES) Model in the Preclinical Assessment of Potential New Antiepileptic Drugs," Methods Find Exp Clin Pharmacol., 2009, 31(2); 101-106.

Charlotte's Web [online], "When to Expect Results from CW Hemp Oil", Mar. 13, 2017, retrieved on May 21, 2018, URL https://www.cwhemp.com/blog/expecting-results-from-hemp, 6 pages.
Charlotte's Web [online], "Whole-Plant Cannabinoids Outperform Single Molecule Compounds," CWHemp.com, Jan. 11, 2017, retrieved on Jun. 16, 2017, URL <https://www.cwhemp.com/blog/whole-plant-cw-hemp-cannabinoids>, 5 pages.
ChildNeurologyFoundation.org [online], "Disorder Directory: Learn from the Experts—LGS (Lennon-Gastaut Syndrome)," Child Neurology Foundation, available on or before Sep. 6, 2005, retrieved on May 21, 2018, URL http://www.childneurologyfoundation.org/disorders/lgs-lennox-gastaut-syndrome, 10 pages.
Chiron and Dulac, "The Pharmacologic Treatment of Dravet Syndrome," Epilepsia, 2011, 52(Suppl. 2): 72-75.
Chiu et al., "The Influence of Cannabidiol and Δ9-Tetrahydrocannabinol on Cobalt Epilepsy in Rats," Epilepsia., 1979, 20:365-375.
Conry et al., "Clobazam in the treatment of Lennox-Gastaut syndrome," Epilepsia, May 2009, 50(5): 1158-1166.
Consroe and Sandyk, "Chapter 12: Potential Role of Cannabinoids for Therapy of Neurological Disorders," Marijuana / Cannabinoids: Neurobiology and Neurophysiology, ed. L. Murphy, 1992, 459-524.
Consroe et al., "Anticonvulsant drug antagonism of $\Delta^9$tetrahydrocannabinol-induced seizures in rabbits," Res Commun Chem Pathol Pharmacol., Jan. 1977, 16(1):1-13.
Consroe et al., "Anticonvulsant Interaction of Cannabidiol and Ethosuximide in Rats," J. Pharm. Pharmac., Aug. 1977, 29(8):500-501.
Consroe et al., "Anticonvulsant Nature of Marihuana Smoking," JAMA, Oct. 1975, 234(3):306-307.
Consroe et al., "Cannabidiol—Antiepileptic Drug Comparisons and Interactions in Experimentally Induced Seizures in Rats," J. Pharm. Exp. Therap., Apr. 1977 , 201(1):26-32.
Consroe et al., "Effects of Cannabidiol on Behavioral Seizures Caused by Convulsant Drugs or Current in Mice," Eur J Pharm, Sep. 1982, 83(3-4):293-298.
Consroe et al., "Chapter 2: Therapeutic Potential of Cannabinoids in Neurological Disorders," Cannabinoids as Therapeutic Agents, R. Mechoulam ed., 1986, 21-49.
Cortesi et al., "Potential therapeutical effects of cannabidiol in children with pharmacoresistant epilepsy," Med Hypotheses., 2007, 68(4):920-921.
Cortez and Snead, "Chapter 10: Pharmacologic Models of Generalized Absence Seizures in Rodents," Models of Seizures and Epilepsy, 2006, 111-126.
Crespel, et al., "Chapter 14: Lennox-Gastaut Syndrome," Epileptic Syndromes in Infancy, Childhood, and Adolescence, 2012, 5th Edition, ed. M. Bureau, 189-216.
Cunha et al., "Chronic Administration of Cannabidiol to Healthy Volunteers and Epileptic Patients," Pharmacology, 1980. 21(3):175-185.
Czapinski et al., "Mar. 17, 2008: Randomized 36-month comparative study of valproic acid (VPA), phenytoin (PHT), phenobarbital (PB) and carbamazepine (CBZ) efficacy in patients with newly diagnosed epilepsy with partial complex seizures," J. Neurol. Sci., Sep. 1997, 150(1):S162-S163.
Dasa et al., "Key Attributes of TKDL: Ganja," Brhat Nighantu Ratnakara (Saligramanighantubhusanam), 1997, 6 pages (with English translation).
Davis and Ramsey, "Antiepileptic action of marihuana-active substances," Federation Proceedings., Mar. 1949, 8:284-285.
Davis et al., "A Predominant Role for Inhibition of the Adenylate Cyclase/Protein Kinase A Pathway in ERK Activation by Cannabinoid Receptor 1 in NIE-115 Neuroblastoma Cells," J Biol Chem., Dec. 2003, 278(49): 48973-48980.
De Meijer, "Chapter 5: The Chemical Phenotypes (Chemotypes) of Cannabis," Handbook of Cannabis, ed. Roger G. Pertwee, 2014, 89-110.
De Oliveira, et al., "Anticonvulsant activity of β-caryophyllene against pentylenetetrazol-induced seizures," Epilepsy Behav, Mar. 2016, 56:26-31.

(56) References Cited

OTHER PUBLICATIONS

Deshpande et al., "Cannabinoid CBI Receptor Antagonists Cause Status Epilepticus-like Activity in the Hippocampal Neuronal Culture Model of Acquired Epilepsy," Neurosci Lett., Jan. 2007, 411: 11-16.
Devinsky et al., "Cannabidiol: Pharmacology and potential therapeutic role in epilepsy and other neuropsychiatric disorders," Epilepsia, 2014, 55(6):791-802.
Dravet, "The core Dravet syndrome phenotype," Epilepsia, Apr. 2011, 52(Suppl 2): 3-9.
Dreifus et al., "Proposal for Revised Clinical and Electroencephalographic Classification of Epileptic Seizures," Epilepsia, Aug. 1981, 22:489-501.
Dulac and Kaminska, "Use of Lamotrigine in Lennox-Gastaut and Related Epilepsy Syndromes," J. Child Neurolog., Nov. 1997, 12(S1): S23-S29.
Dulac et al., "Vigabatrin in Childhood Epilepsy," J. Child Neurolog., 1991, 6(S2): S30-S37.
Eadie, "Shortcomings in the current treatment of epilepsy," Expert Rev Neurother., Dec. 2012, 12(12): 1419-1427.
Eggers, "Temporal lobe epilepsy is a disease of faulty neuronal resonators rather than oscillators, and all seizures are provoked, usually by stress," Med Hypotheses, 2007, 69(6): 1284-1289.
ElSohly and Gul, "Chapter 1: Constituents of Cannabis Sativa," Handbook of Cannabis, 2014, ed. Roger G. Pertwee, 3-22.
Engel et al., "Chapter 1: What Should be Modeled?," In Models Seizure Epilepsy., 2006, 14 pages.
Engel, "Report of the ILAE Classification Core Group," Epilepsia, 2006, 47(9): 1558-1568.
EPO Annex to the Communication in Opposition for European Appln. No. 10734541.5, dated Jan. 28, 2016, 5 pages.
EPO Auxiliary Requests to the File in European Patent No. EP2448637, dated Nov. 2, 2016, 45 pages.
EPO Communication of a Notice of Opposition in European Appln. No. 10734541.5, dated Dec. 17, 2014, 1 page.
EPO Communication Pursuant to Article 94(3) EPC in European Appln. No. 10734541.5, dated Oct. 23, 2012, 3 pages.
EPO Interlocutory Decision in Opposition in European Appln. No. EP2448637, dated Dec. 15, 2016, 91 pages.
EPO Letter from Opponent Regarding Oral Proceedings in European Patent No. EP2448637, dated Oct. 20, 2016, 6 pages.
EPO Notice of Appeal in European Patent No. EP2448637, dated Feb. 14, 2017, 5 pages.
EPO Notice of Opposition to a European Patent No. EP2448637, Dated Dec. 5, 2014, 20 pages.
EPO Opponent Response to the Preliminary Opinion of the Opposition Division in European Patent No. EP2448637, dated Jun. 23, 2016, 27 pages.
EPO Opponent Response to the Preliminary Opinion of the Opposition Division in European Patent No. EP2448637, dated Sep. 9, 2016, 25 pages.
EPO Opponent Response to the Written Submissions in European Patent No. EP2448637, dated Oct. 12, 2016, 18 pages.
EPO Opponent Response to the Written Submissions in European Patent No. EP2448637, dated Oct. 20, 2016, 3 pages.
EPO Opponent Written Submission in European Patent No. EP2448637, dated Nov. 4, 2016, 3 pages.
EPO Opposition, Expert Statement of Dr. Emma Louise Cheetham in European Appln. No. EP10734541.5, dated Nov. 4, 2016, 1 pages.
EPO Opposition, Expert Statement of Professor Anthony G Marson in European Appln. No. EP10734541.5 , dated Jun. 14, 2016, 9 pages.
EPO Opposition, Expert Statement of Professor Benjamin J. Whalley in European Appln. No. EP10734541.5, dated Sep. 9, 2016, 11 pages.
EPO Opposition, Expert Statement of Vincenzo Di Marzo in European Appln. No. EP10734541.5, dated Sep. 9, 2016, 10 pages.
EPO Opposition, Supplemental Expert Statement of Professor Benjamin J. Whalley, dated Nov. 4, 2016, 9 pages.
EPO Reply of the Patent Proprietor to the Notice(s) of Opposition in European Patent No. 2448637, dated May 28, 2015, 12 pages.
EPO Reply to Examination Report in European Patent Application No. 10734541.5, dated Feb. 15, 2013, 54 pages.
EPO Reply to Opponent's Written Submission in European Patent No. EP2448637, dated Nov. 4, 2016, 13 pages.
EPO Reply to Opponent's Written Submissions in European Patent No. EP2448637, dated Oct. 18, 2016, 5 pages.
EPO Reply to Preliminary Opinion and Opponent's Observations in European Patent No. EP2448637, dated Sep. 9, 2016, 65 pages.
EPO Reply to Proprietor's Statement of Grounds of Appeal in European Patent No. EP2448637, dated Sep. 8, 2017, 5 pages.
EPO Response to the Statement of Grounds of Appeal in European Patent No. 2448637, dated Sep. 5, 2017, 17 pages.
EPO Statement of Grounds of Appeal in European Appln. No. 10734541.5 , dated Apr. 21, 2017, 14 pages.
EPO Statement of Grounds of Appeal in European Appln. No. 10734541.5, dated Apr. 12, 2017, 6 pages.
EPO Statement of Opposition in European Appln. No. EP10734541.5, dated Dec. 5, 2014, 14 pages.
EPO Third Party Observations in European Appln. No. EP10734541.5, dated Apr. 3, 2017, 19 pages.
EPO Third Party Observations in European Appln. No. EP11712658.1, dated Nov. 22, 2013, 14 pages.
Fariello, "Parenteral Penicillin in Rats: An Experimental Model of Multifocal Epilepsy," Epilepsia, 1976, 17:217-222.
FDA [online], "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
FDA [online], "Warning Letters and Test Results for Cannabidiol-Related Products," 2016 Warning Letters, retrieved on Nov. 14, 2017, URL <https://www.fda.gov/newsevents/publichealthfocus/ucm484109.htm> , 4 pages.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Ferdinand et al., "Cannabis—Psychosis Pathway Independent of Other Types of Psychopathology," Schizophrenia Research, 2005, 79:289-295.
Fisher et al., "The impact of epilepsy from the patient's perspective I. Descriptions and subjective perceptions," Epilepsy Research, 2000, 41(1):39-51.
Gabor et al., "Lorazepam Versus Phenobarbital: Candidates for Drug of Choice for Treatment of Status Epilepticus," J Epilepsy, Jan. 1990, 3(1):3-6.
Gallily et al., "Overcoming the Bell-Shaped Dose-Response of Cannabidiol by Using Cannabis Extract Enriched in Cannabidiol," Pharmacology & Pharmacy, Jan. 2015, 6:75-85.
Gardner [online], "Comes Now Epidiolex (FDA Approves IND Studies of CBD)," BeyondTHC.com, Oct. 22, 2013, retrieved on Jan. 31, 2018, URL <http://www.beyondthc.com/comes-now-epidiolex-fda-approves-ind-studies-of-cbd>, 4 pages.
Gastaut., "Clinical and Electroencephalographical Classification of Epileptic Seizures," Epilepsia, 1970, 11:102-113.
GB Combined Search and Examination Report in GB Appln. No. GB1116789.7, dated Jan. 4, 2012, 8 pages.
GB Combined Search and Examination Report in Application No. GB1611544.6, dated Mar. 29, 2017, 8 pages.
GB Combined Search and Examination Report in GB Appln. No. GB1100043.7, dated Mar. 25, 2011, 8 pages.
GB Combined Search and Examination Report in GB Appln. No. GB1121919.3, dated Feb. 29, 2012, 8 pages.
GB Combined Search and Examination Report in GB Appln. No. GB1410771.8, dated Feb. 27, 2015, 7 pages.
GB Combined Search and Examination Report in GB Appln. No. GB1414813.4, dated Sep. 5, 2014, 8 pages.
GB Combined Search and Examination Report in GB Appln. No. GB1418166.3, dated Jul. 2, 2015, 8 pages.
GB Combined Search and Examination Report in GB Appln. No. GB1418170.5, dated Jul. 2, 2015, 6 pages.

(56) References Cited

OTHER PUBLICATIONS

GB Combined Search and Examination Report in GB Appln. No. GB1418171.3, dated Jun. 29, 2015, 8 pages.
GB Combined Search and Examination Report in GB Appln. No. GB1506550.1, dated Feb. 5, 2016, 9 pages.
GB Combined Search and Examination Report in GB Appln. No. GB1514079.1, dated May 4, 2016, 9 pages.
GB Combined Search and Examination Report in GB Appln. No. GB 1605448.8, dated Jan. 12, 2017, 6 pages.
GB Examination Report in GB Appln, No. GB1100043.7, dated Mar. 18, 2014, 2 pages.
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde_presentation.pdf, Sep. 9-11, 2014>, 45 pages.
Gedde et al., "3.330: Whole Cannabis Extract of High Concentration Cannabidiol May Calm Seizures in Highly Refractory Pediatric Epilepsies," American Epilepsy Society, Dec. 2013, 449-450.
Geffrey et al., "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.
Green [online], "CBD: An Unconventional Therapy," Nugs.com, Mar. 24, 2014, URL <http://nugs.com/article/cbd-an-unconventional-therapy.html>, 5 pages.
Gresham et al., "Treating Lennox-Gastaut syndrome in epileptic pediatric patients with third generation rufinamide," Neuropsychiatr Dis Treat, Oct. 5, 2010, 6:639-645.
Gross et al., "Marijuana use and Epilepsy: Prevalence in Patients of a Tertiary Care Epilepsy Center," Neurology, Jun. 8, 2004, 62(11):2095-2097.
Guerrini et al., "Lamotrigine and Seizure Aggravation in Severe Myoclonic Epilepsy," Epilepsia, 1998, 39(5):508-512.
Guimaraes et al., "Antianxiety effect of cannabidiol in the elevated plus-maze," Psychopharmacology, 1990, 100: 558-559.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL <https://www.gwpharm.com/about-us/news/gw-pharmaceuticals-announces-epidiolex%C2%AE-receives-fast-track-designation-fda-treatment>, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.
GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.
GWPharm [online], "GW Pharmaceuticals Receives Orphan Drug Designation by FDA for Epidiolex® in the Treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.
Heinemann et al., "Chapter 4: An Overview of In Vitro Seizure Models in Acute and Organotypic Slices," Models of Seizures and Epilepsy, 2006 35-44.
Hill et al., "$\Delta^9$-Tetrahydrocannabivarin suppresses in vitro epileptiform and in vivo seizure activity in adult rats," Epilepsia, Aug. 2010, 51(8):1522-1532.
Hill, "Cannabidivarin-rich cannabis extracts are anticonvulsant in mouse and rat via a CB1 receptor-independent mechanism," British Journal of Pharmacology, Oct. 2013, 170(3): 679-692.
Holmes et al. "Choosing the Correct AED: From Animal Studies to the Clinic," Pediatr Neurol, Mar. 2008, 38(3): 151-162.
Iannotti et al., "Nonpsychotropic plant cannabinoids, cannabidivarin (CBDV) and cannabidiol (CBD), activate and desensitize transient receptor potential vanilloid 1 (TRPV1) channels in vitro: Potential for the treatment of neuronal hyperexcitability," ACS Chem. Neurosci., Jul. 16, 2014, 5:1131-1141.
ICE Epilepsy Alliance, The Dravet Syndrome Spectmm, Nov. 2008, 2 pages.
*Insys Development Company, Inc.* v. *GW Pharma Limited and Otsuka Pharmaceutical Co., Ltd.*, Decision in IPR2017-00503, U.S. Pat. No. 9,066,920, dated Jul. 7, 2017, 26 pages.
*Insys Development Company, Inc.* v. *GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*Insys Development Company, Inc.* v. *GW Pharma Limited and Otsuka Pharmaceutical Co., Ltd.*, Declaration of Professor Anthony G. Marson in IPR2017-00503, U.S. Pat. No. 9,066,920, dated Dec. 13, 2016, 28 pages.
*Insys Development Company, Inc.* v. *GW Pharma Limited and Otsuka Pharmaceutical Co., Ltd.*, Declaration of Professor H. Steve White in IPR2017-00503, U.S. Pat. No. 9,066,920, dated Oct. 24, 2017, 69 pages.
*Insys Development Company, Inc.* v. *GW Pharma Limited and Otsuka Pharmaceutical Co., Ltd.*, Declaration of Professor Leslie Benet in IPR2017-00503, U.S. Pat. No. 9,066,920, dated Nov. 22, 2016, 18 pages.
*Insys Development Company, Inc.* v. *GW Pharma Limited and Otsuka Pharmaceutical Co., Ltd.*, Deposition of H. Steve White, dated Dec. 13, 2016, 50 pages.
*Insys Development Company, Inc.* v. *GW Pharma Limited and Otsuka Pharmaceutical Co., Ltd.*, Final Written Decision in IPR2017-00503, U.S. Pat. No. 9,066,920, dated Jan. 3, 2019, 40 pages.
*Insys Development Company, Inc.* v. *GW Pharma Limited and Otsuka Pharmaceutical Co., Ltd.*, Patent Owners' Preliminary Response in IPR2017-00503, U.S. Pat. No. 9,066,920, dated Apr. 11, 2017, 45 pages.
*Insys Development Company, Inc.* v. *GW Pharma Limited and Otsuka Pharmaceutical Co., Ltd.*, Petition for Inter Partes Review, IPR2017-00503, U.S. Pat. No. 9,066,920, dated Dec. 16, 2016, 78 pages.
*Insys Development Company, Inc.* v. *GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*Insys Development Company, Inc.* v. *GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.
*Insys Development Company, Inc.* v. *GW Pharma Limited and Otsuka Pharmaceutical Co., Ltd.*, Petitioner's Reply to Response in IPR2017-00503, U.S. Pat. No. 9,066,920, dated Jan. 19, 2018, 36 pages.
IUPHAR/BPS Guide to Pharmacology [online], "Entry for $\Delta$9-tetrahydrocannabidiol," available on or before Mar. 29, 2016, retrieved on Jun. 20, 2018, URL <http://www.guidetopharmacology.org/GRAC/LigandDisplayForward?tab=biology&ligandId=242>, 2 pages.

(56) References Cited

OTHER PUBLICATIONS

Iuvone et al., "Neuroprotective Effect of Cannabidiol, a Non-psychoactive Component From Cannabis Sativa, on β-amyloid-induced toxicity in PC12 Cells," J Neurochem, Apr. 2004, 89(1):134-41.

Izzo et al., "Non-psychotropic plant cannabinoids: new therapeutic opportunities from an ancient herb," Trends in Pharmacological Sciences, 2009, 30(10):515-527.

Jacobson and Porter, "Survey of Current Cannabidiol Use in Pediatric Treatment-Resistant Epilepsy", Apr. 2013, URL <https://www.thcint.com/uploads/1/9/3/7/19371199/cannabidiol_use_in_pediatric_epilepsy.pdf>. 1 page.

Jeavons et al., "Sodium Calproate in Treatment of Epilepsy," Br Med J., Jun. 15, 1974, 2(5919):584-586.

Jones et al. [online], Info & Metrics / Article Information, "Cannabidiol Displays Antiepileptiform and Antiseizure Properties in Vitro and in Vivo," J Pharmacol Exp Ther., Feb. 2010, 332(2):569-577, retrieved on Jun. 25, 2018, URL: http://jpet.aspetjournals.org/content/332/2/569/tab-article-info, 9 pages.

Jones et al., "Cannabidiol Displays Antiepileptiform and Antiseizure Properties in Vitro and in Vivo," J Pharmacol Exp Ther., Feb. 2010, 332(2):559-577.

Joy et al., "Marijuana and Medicine: Assessing the Science Base", Institute of Medicine, National Academy Press, 1999, 170 pages.

Kahan et al., "Risk of Selection Bias in Randomized Trials," Trials, Sep. 2015, 16:405, 7 pages.

Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.

Karler et al., "The Cannabinoids as Potential Antiepileptics," J Clin Pharmacol., Aug.-Sep. 1981, 21:437S-448S.

Kelley et al., "Doose syndrome (myoclonic-astatic epilepsy): 40 years of progress," Developmental Medicine & Child Neurology, Aug. 2010, 52: 988-993.

Khan et al., "Key Attributes of TKDL: Laooq-e-Qinnab/Barai Zeequn-Nafs," Khazaain-al-Advia, 1911, 2 pages (with English translation).

Khan et al., "Key Attributes of TKDL: Nuskha-e-Qutoor," Muheet-e-Azam, 1887, 2 pages (with English translation).

Khan et al., "Key Attributes of TKDL: Sufoof-e-qinnab Barae Waja," Khazaain-al-Adiva, 1911, 5 pages (with English translation).

Khan et al., "Key Attributes of TKDL: Usaara-e-Qinnab Barai Qoolanj," Khazaain-al-Advia, 1911, 6 pages (with English translation).

Khan et al., "Key Attributes of TKDL: Zimad-e-qinnab," Khazaain-al-Adiva, 1911, 5 pages (with English translation).

Klitgaard et al., "Electrophysiological, neurochemical and regional effects of levetiracetam in the rat pilocarpine model of temporal lobe epilepsy," Seizure, Mar. 2003, 12(2):92-100.

Klitgaard et al., "Evidence for a unique profile of levetiracetam in rodent models of seizures and epilepsy," European J Pharm, Jul. 1998, 353(2)491-206.

Kramer et al., "Febrile infection-related epilepsy syndrome (FIRES): pathogenesis, treatment, and outcome: a multicenter study on 77 children," Epilepsia, Nov. 2011, 52(11):1956-1965.

Kwan et al., "Definition of drag resistant epilepsy: consensus proposal by the ad hoc Task Force of the ILAE Commission on Therapeutic Strategies," Epilepsia, Jun. 2010, 51(6):1069-1077.

LeafScience.com [online], "What are the Highest CBD Strains?" Oct. 15, 2014, retrieved on Feb. 16, 2017, URL <www.leafscience.com/2014/10/15/highest-cbd-strains/>, 2 pages.

Leo et al., "Cannabidiol and epilepsy: Rationale and therapeutic potential," Pharamacological Research, Mar. 2016, 107: 85-92.

Lewis, "Mystery Mechanisms," TheScientist.com, Jul. 29, 2016, retrieved on Nov. 8, 2017, URL <https://www.the-scientist.com/?articles.view/articleNo/46688/title/Mystery-Mechanisms/>, 2 pages.

Lieu et al., "Assessment of self-selection bias in a pediatric unilateral hearing loss study," Otolaryngol Head Neck Surg, Mar. 2010, 142(3): 427-433.

Lindamood and Colasanti, "Effects of $\Delta^9$-Tetrahydrocannabinol and Cannabidiol on Sodium-Dependent High Affinity Choline Uptake in the Rat Hippocampus1," J Pharmacology Experimental Therapeutics, 1980, 213(2):216-221.

Long et al., "The Pharmacological actions of cannabidiol," Drugs of the Future, Jul. 2005, 30(7):747-753.

Löscher and Schmidt, "Modern antiepileptic drug development has failed to deliver: ways out of the current dilemma." Epilepsia, Apr. 2011, 52(4):657-78.

Lowenstein "Chapter 363: Seizures and Epilepsy," Diseases of the Central Nervous System, 2008, 2498-2512.

Luttjohann et al., "A Revised Racine's scale for PTZ-induced seizures in rats," Physiology & Behavior, 2009, 98:579-586.

Lutz, "On-demand activation of the endocannabinoid system in the control of neuronal excitability and epileptiform seizures," Biochemical Pharmacology, Nov. 2004, 68(9):1691-1698.

Maa et al., "The Case for Medical Marijuana in Epilepsy," Epilepsia, Jun. 2014, 55(6):783-786.

Mackie, "Cannabinoid Receptors as Therapeutic Targets," Annu Rev Pharmacol Toxicol, 2006, 46:101-122.

Majoosi et al., "Key Attributes of TKDL: Saoot Baraae Sara," Kaamil-al-Sena'ah, Central Council for Research in Unani Medicine, 2005, 2 pages (with English translation).

Malfait et al., "The nonpsychoactive cannabis constituent cannabidiol is an oral anti-arthritic therapeutic in murine collagen-induced arthritis," PNAS, Aug. 15, 2000, 97(17):9561-9566.

Manni et al., "Obstructive Sleep Apnea in a Clinical Series of Adult Epilepsy Patients: Frequency and Features of the Comorbidity," Epilepsia, Jun. 2003, 44(6): 836-840.

Manno, "Status Epilepticus: Current Treatment Strategies," The Neurohospitalist, Jan. 2011, 1(1):23-31.

Mares et al., "Chapter 12: Electrical Stimulation-Induced Models of Seizures," Model of Seizures and Epilepsy, Asla Pitkänen, Philip A. Schwartzkroin & Solomon L. Moshé, eds., 2004, 153-159.

Martin et al., "Structure-Anticonvulsant Activity Relationships of Cannabidiol Analogs," National Institute on Drug Abuse, Research Monograph Series, 1987, 79:48-58.

Mattson et al., "Comparison of carbamazepine, phenobarbital, phenytoin, and primidone in partial and secondarily generalized tonic-clonic seizures," N Engl J Med, Jul. 18, 1985, 313(3):145-151.

Mattson et al., "Prognosis for total control of complex partial and secondary generalized tonic clonic seizures," Neurology, 1996, 47:68-76.

McCormick et al., "On the Cellular Network Bases of Epileptic Seizures," Annu Rev Physiol, 2001, 63:815-846.

McNamara, "Chapter 19: Pharmacotherapy of the Epilepsies,", Goodman & Gilman's The Pharmacological Basis of Therapeutics 11th ed., McGraw-Hill Companies, 2006, 501-525.

Mechoulam et al., "Cannabidiol: An Overview of Some Pharmacological Aspects," J Clin Pharmacol, 2002, 42:11S-19S.

Mechoulam et al., "Toward drugs derived from cannabis," Naturwissenschaften, Apr. 1978, 65(4):174-179.

Medicos [online], "Convulsive Disorders and Their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving/>, 3 pages.

Merlis, "Proposal for an International Classification of the Epilepsies," Epilepsia, 1970, 11:114-119.

Miller et al., "Mapping genetic modifiers of survival in a mouse model of Dravet syndrome," Genes, Brain and Behavior, 2014, 13:163-172.

Moral et al., "Pipeline on the Move," Drugs of the Future, Jan. 2014, 39(1): 49-56.

Morard et al., "Conversion to Sirolimus-Based Immunosuppression in Maintenance Liver Transplantation Patients," Liver Transplantation, 2007, 13:658-664.

MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.

Neto et al., "The role of polar phytocomplexes on anticonvulsant effects of leaf extracts of Lippia Alba (Mill.) N.E. Brown chemotypes," J. Pharm Pharmacol, 2009, 61(7):933-939.

(56) References Cited

OTHER PUBLICATIONS

Ng et al., "Illicit Drug Use and the Risk of New-Onset Seizures," Am J Epidemiol, 1990, 132(1):47-57.
Oakley et al., "Dravet Syndrome Insights into pathophysiology and therapy from a mouse model of Dravet syndrome," Epilepsia, Apr. 2011, 52(Suppl. 2): 59-61.
Obay et al., "Antiepileptic effects of ghrelin on pentylenetetrazole-induced seizures in rats," Peptides, Jun. 2007, 28(6):1214-1219.
PCT International Preliminary Report on Patentability in International Appln. No. PCT/GB2010/051066, dated Jun. 9, 2011, 6 pages.
PCT International Preliminary Report on Patentability in International Appln. No. PCT/GB2012/052284, dated Dec. 12, 2013, 12 pages.
PCT International Preliminary Report on Patentability in International Appln. No. PCT/GB2015/051775, dated Aug. 10, 2016, 9 pages.
PCT International Preliminary Report on Patentability in International Appln. No. PCT/GB2015/053030, dated Apr. 18, 2017, 6 pages.
PCT International Preliminary Report on Patentability in International Appln. No. PCT/GB2016/051792, dated Sep. 1, 2017, 14 pages.
PCT International Preliminary Report on Patentability in International Appln. No. PCT/US2017/050868, dated Oct. 11, 2018, 7 pages.
PCT International Search Report and Written Opinion in International Appln. No. PCT/GB2010/051066 dated Dec. 13, 2010, 8 pages.
PCT International Search Report and Written Opinion in International Appln. No. PCT/GB2011/050649, dated May 30, 2011, 15 pages.
PCT International Search Report and Written Opinion in International Appln. No. PCT/GB2012/052284, dated Nov. 16, 2012, 11 pages.
PCT International Search Report and Written Opinion in International Appln. No. PCT/GB2015/051775, dated Aug. 26, 2015, 11 pages.
PCT International Search Report and Written Opinion in International Appln. No. PCT/GB2015/051776, dated Aug. 25, 2015, 11 pages.
PCT International Search Report and Written Opinion in International Appln. No. PCT/GB2016/052340, dated Oct. 25, 2016, 12 pages.
PCT International Search Report and Written Opinion in International Appln. No. PCT/US2017/050868, dated Aug. 6, 2017, 14 pages.
PCT International Search Report and Written Opinion in International Appln. PCT/GB2017/051943, dated Sep. 12, 2017, 10 pages.
PCT International Search Report in International Appln. No. PCT/GB2012/050002, dated Feb. 24, 2012, 3 pages.
PCT Interntional Search Report and Written Opinion in International Appln. No. PCT/GB2017/051913, dated Sep. 15, 2017, 9 pages.
PCT Interntional Search Report and Written Opinion in International Appln. No. PCT/GB2017/051914, dated Sep. 12, 2017, 10 pages.
Pelliccia et al. [online], "Treatment with CBD in oily solution of drag-resistant paediatric epilepsies," 2005 Congress on Cannabis and the Cannabinoids, Leiden, The Netherlands: International Association for Cannabis as Medicine, 2005, 14, retrieved on Jun. 30, 2015, URL <http://www.cannabis-med.org/studies/ww_en_db_study_show.php?s_id=173&&search_pattern=EPILEPSY>, 2 pages, Abstract only.
Pereira et al., "Study pharmacologic of the GABAergic and glutamatergic drags on seizures and status epilepticus induced by pilocarpine in adult Wistar rats," Neurosci Lett, Jun. 2007, 419(3):253-257.

Pertwee, "Cannabinoid receptor ligands: clinical and neuropharmacological considerations, relevant to future drug discovery and development," Expert Opin Investig Drugs, Jul. 2000, 9(7): 1553-1571.
Pertwee, "Chapter 3: The Pharmacology and Therapeutic Potential of Cannabidiol," Cannabinoids, Ed Vincenzo Di Marzo ed., 2004, 32-83.
Pertwee, "The diverse CB1 and CB2 receptor pharmacology of three plant cannabinoids: Δ9-tetrahydrocannabinol, cannabidiol and Δ9-tetrahydrocannabivarin," Br. J. Pharmacol, 2008, 153(2):199-215.
Petrocellis et al., "Effects of cannabinoids and cannabinoid-enriched Cannabis extracts on TRP channels and endocannabinoid metabolic enzymes," British Journal of Pharmacology, 2011, 163:1479-1494.
Pohl et al., "Effects of flunarizine on Metrazol-induced seizures in developing rats," Epilepsy Res, 1987, 1:302-305.
Poortman-van der Meer, "A contribution to the improvement of accuracy in the quantitation of THC," Forensic Science International, Apr. 1999, 101(1): 1-8.
Porter et al., "Randomized, multicenter, dose-ranging trial of retigabine for partial-onset seizures," Neurology, Apr. 2007, 68(15): 1197-1204.
Porter et al., "Report of a Parent Survey of Cannabidiol-enriched Cannabis use in Pediatric Treatment-resistant Epilepsy," Epilepsy Behavior, Dec. 2013, 29(3): 574-577.
Potter, "Chapter 4: Cannabis Horticulture," Handbook of Cannabis, ed. Roger G. Pertwee, 2014, 65-88.
Ponton, "Lipid formulations for oral administration of drugs: non-emulsifying, self-emulsifying and 'self-microemulsifying' drug delivery systems," Eur. J Pharm Sci, Oct. 2000, 11(Supp. 2): S93-S98.
Press et al., "Parental reporting of response to oral cannabis extracts for treatment of refractory epilepsy," Epilepsy Behav, Apr. 2015, 45:49-52.
Pruitt et al., "Ethanol in Liquid Preparations Intended for Children," Pediatrics, Mar. 1984: 73(3): 405-407.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi—Goutieres syndrome," Official J Eur Paediatric Neurology Society, 2014, 18: 30-37.
Rauca et al., "The role of superoxide dismutase and a-tocopherol in the development of seizures and kindling induced by pentylenetetrazol—influence of the radical scavenger a-phenyl-N-tert-butyl nitrone," Brain Research, May 29, 2004 , 1009(1-2):203-212.
Resstel et al., "5-$HT_{1A}$ receptors are involved in the cannabidiol-induced attenuation of behavioural and cardiovascular responses to acute restraint stress in rats," Br J Pharmacol, Jan. 2009, 156(1):181-188.
Rosenberg et al., "Cannabinoids and Epilepsy," Neurotherapeutics, Oct. 2015, 12(4): 747-768.
Rosenkrantz et al., "Oral and Parenteral Formulations of Marijuana Constituents," J Pharm Sci, Jul. 1972, 61(7)1106-1112.
Rubio et al., "In Vivo Experimental Models of Epilepsy," Central Nervous System Agents in Medicinal Chemistiy, 2010, 10:298-309.
Russo, "Taming THC: potential cannabis synergy and phytocannabinoid-terpenoid entourage effects," British J. of Pharm, 2011, 163:1344-1364.
Sadanandasarma et al., "Key Attributes of TKDL: Suddha Bhanga Visista Gunah Aur Matra," Rasatarangini 11th Ed., 1979:720-723 (with English translation).
SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.com/cannabidiol-aicardi-syndrome/>, 3 pages.
Sander, "The epidemiology of epilepsy revisited," Curr Opin Neurol, Apr. 2003, 16(2):165-170.
Sastri et al., "Key Attributes of TKDL: Vijaya Kalpah (Apasmaranasaka)," Anandakandam 1st ed., 1952:241, 5 pages (with English translation).
Scuderi et al., "Cannabidiol in Medicine: A Review of its Therapeutic Potential in CNS Disorders," Phytother Res, May 2009, 23(5):597-602.

(56) References Cited

OTHER PUBLICATIONS

Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., "Clobazam as Add-on Therapy in Children with Epileptic Encephalopathy," Can J Neurol Sci, 2006 33: 209-213.
Sperling et al., "Carisbamate as adjunctive treatment of partial onset seizures in adults in two randomized, placebo-controlled trials," Epilepsia, Mar. 2010, 51(3):333-343.
Stafstrom et al., "Models of Pediatric Epilepsies: Strategies and Opportunities," Epilepsia, 2006, 47(8): 1407-1414.
Stephenson, "In Memoriam: Professor Jean Aicardi (1926-2015)," Pediatric Neurology, Jan. 2016, 54: 3-4.
Stott et al., "Cannabinoids for the pharmaceutical industry," Euphytica, 2004, 140:83-93.
Strickley, "Solubilizing Excipients in Oral and Injectable Formulations," Table VIII, Pharmaceutical Research, Feb. 2004, 21(2): 201-230.
Swann., "The Effects of Seizures on the Connectivity and Circuitry of the Developing Brain," MRDD, 2004, 10(2):96-100.
Thomas et al., "Evidence that the Plant Cannabinoid Δ9-Tetrahydrocannabivarin is a Cannabinoid CB1 and CB2 Receptor antagonist," Br J Pharmacol, Dec. 2005, 146(7):917-926.
Thumma et al., "Influence of plasticizers on the stability and release of a prodrug of Δ9-tetrahydrocannabinol incorporated in poly (ethylene oxide) matrices," Eur J Pharmceutics and Biopharmaceutics, Oct. 2008, 70(2): 605-614.
Thurman et al., "Standards for epidemiologic studies and surveillance of epilepsy," Epilepsia, Sep. 2011, 52 Suppl 7: 2-26.
Thurstone, "Avoid Charlotte's Web for Epilepsy," Jun. 26, 2014, URL <http://drthurstone.com/charlotted-web-not-safest-option-epiliepsy-treatment/>, 4 pages.
Trembly and Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract Only.
Turkanis et al., "An Electrophysiological Analysis of the Anticonvulsant Action of Cannabidiol on Limbic Seizures in Conscious Rats," Epilepsia, 1979, 20:351-363.
Unimed Pharmaceuticals, Inc., "Marinol®," Jul. 2006 <https://www.accessdata.fda.gov/drugsatfda_docs/label/2006/018651s025s0261bl.pdf>, 11 pages.
Usami et al., "Synthesis and Pharmacological Evaluation in Mice of Halogenated Cannabidiol Derivatives," Chem Pharm Bull, Nov. 1999, 47(11):1641-1645.
USPTO Decision on Appeal in U.S. Appl. No. 10/318,659 (Appeal 2009-011751), dated Jul. 8, 2010, 23 pages.
USPTO Decision on Appeal in U.S. Appl. No. 13/698,730 (Appeal 2016-006358), dated Jun. 21, 2017, 6 pages.
USPTO Information Disclosure Statement Form PTO-1449 in U.S. Appl. No. 13/380,305, dated Nov. 24, 2014, 8 pages.
USPTO Notice of Allowance in U.S. Appl. No. 13/380,305, dated Dec. 10, 2014, 5 pages.
USPTO Notice of Allowance in U.S. Appl. No. 13/380,305, dated Mar. 19, 2015, 7 pages.
USPTO Office Action in U.S. Appl. No. 13/380,305, dated Aug. 25, 2014, 6 pages.
USPTO Request for Continued Examination with the Amendment and Information Disclosure Statement in U.S. Appl. No. 13/380,305, filed Mar. 2, 2015, 8 pages.
USPTO Third Preliminary Amendment under 37 C.F.R. 1.115 in U.S. Appl. No. 13/380,305, dated May 23, 2014, 4 pages.
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent findings," Neuropsychiatr Dis Treat, Dec. 2008, 4(6): 1001-1019.
Velisek, "Chapter 11: Models of Chemically-Induced Acute Seizures," Models of Seizures and Epilepsy, 2006, 127-152.
Veliskova, "Chapter 48: Behavioral Characterization of Seizures in Rats," Models Seizures Epilepsy, 2006, 601-611.
Vollner et al., "Haschisch XX+ [Haschiscc XX+]: Cannabidivarin, a new hashish substance," Tetrahedron Letters, 1969, 10(3):145-147.
Wahle et al., "Development of Tolerance to the Anticonvulsant Effect of Valproate but not to Ethosuximide in a Rat Model of Absence Epilepsy," Eur J Pharma, May 1990, 181(1-2): 1-8.
Wallace et al., "Assessment of the role of CB1 receptors in cannabinoid anticonvulsant effects," European J Pharmacology, 2001, 428(1):51-57.
Wallace et al., "Pharmacotherapy for Dravet syndrome," Pediatr. Drugs, Jun. 2016, 18:197-208.
Weston et al., "Tetrahydrocannabivarin Exhibits Anticonvulsant Effects in a Piriform Cortical Brain Slice Model of Epileptiform Activity," Proceedings of the British Pharm Society, Dec. 2006, retrieved on Mar. 1, 2017, URL <http://www.pA2online.org/abstract/abstract.jsp?abid=28533>, 1 page, Abstract Only.
Wikipedia.org [online], "Cannabinoid," Wikipedia, Apr. 2003, retrieved on Mar. 1, 2017, URL <https://en.wikipedia.org/wiki/Cannabinoid>, 15 pages.
Wingerchuk, "Cannabis for medical purposes: cultivating science, weeding out the fiction," Lancent, Jul. 2004, 364:315-316.
Yu et al., "Reduced sodium current in GABAergic interneurons in a mouse model of severe myoclonic epilepsy in infancy," Nature Neuroscience, Sep. 2006, 9(9): 1142-1149.
Yuriev, "Endogenic Cannabinoid System is a New Perspective Object of Pharmacotherapeutic Effect to Disease of Nervous System," Ukrainsky Metodichny Chasopis, 2005, 6(50): 21-29 (with English Abstract).
Zhao et al., "Chapter 27: Repetitive Seizures in the Immature Brain," Models of Seizures and Epilepsy, 2006, 341-350.
Zhornitsky and Potvin, "Cannabidiol in Humans—The Quest for Therapeutic Targets," Pharmaceuticals, 2012, 5:529-552.
Zuardi et al., "Cannabidiol, a Cannabis sativa constituent, as an antipsychotic drug," Brazilian Journal of Medicine and Biological Research, Apr. 2006, 39(4): 421-429.
Zuardi et al., "Cannabidiol: from an inactive cannabinoid to a drug with wide spectrum of action," Rev Bras Psiquiatr, 2008, 30(3): 271-80.
[No Author Listed], Cannabinoid. Wikipedia. Retrieved on Jul. 9, 2015 from https://en.wikipedia.org/wiki/Cannabinoid, 15 pages.
Astruc-Diaz, F., "Cannabinoids delivery systems based on supramolecular inclusion complexes and polymeric nanocapsules for treatment of neuropathic pain," Université Claude Bernard—Lyon I, 2012, submitted on Jan. 23, 2014; https://tel.archives-ouvertes.fr/tel-00935588 [accessed Nov. 1, 2019].
Benowitz & Jones, "Cardiovascular and metabolic considerations in prolonged cannabinoid administration in man," J Clin Pharm, 21:214S-223S (1981).
Consroe et al., "Controlled clinical trial of cannabidiol in Huntington's Disease," Pharmacology Biochemistry & Behavior, 40:701-708 (1991).
Curia et al., "The pilocarpine model of temporal lobe epilepsy," J Neuroscience Methods, 172(2-4):143-157 (2008).
Grotenhermen, "Epilepsiebehandlung des Angelman-Syndromes mit CBD (Cannabidiol) (Epilepsy treatment of Angelman syndrome with CBD (cannabidiol)," Angelman e. V., Jan. 2015, retrieved on Jun. 7, 2019, URL <http://s8a5e4d6fcfb04b6.jimcontent.com/download/version//1472724876/module/9873059694/name/Epilepsiebehandlung%20durch%20CBD.pdf> (with Machine English translation), 8 pages.
Karler et al., "The anticonvulsant activity of cannabidiol and cannabinol," Life Science, 13:1527-1531 (1973).
Kruk-Slomka et al., "A comparison of mecamylamine and bupropion effects on memory-related responses induced by nicotine and scopolamine in the novel object recognition test in mice," Pharmacological Reports, 66(4):638-646 (2014).
Kurz & Blass, "Use of dronabinol (delta-9-THC) in autism: A prospective single-case-study with an early infantile autistic child," Cannabinoids, 5(4):4-6 (2010).

(56) References Cited

OTHER PUBLICATIONS

LaPrarie et al., "Cannabidiol is a negative allosteric modulator of the cannabinoid CB1 receptor," British J Pharmacology, 172(20):4790-4805 (2015).

Physician's Desk Reference, 63rd Ed., 2009, 423-461, 2192-2194, 2639-2242, 3019-3022.

Sandyk et al., "Preliminary trial of cannabidiol in Huntington's Disease," Marihuana: An International Research Report, 157-162 (1988).

Zamberletti et al., "Alterations of prefrontal cortex GABAergic transmission in the complex psychotic-like phenotype induced by adolescent delta-9-tetrahydrocannabinol exposure in rats," Neurobiology of Disease, 63:35-47 (2014).

* cited by examiner

ORAL CANNABINOID FORMULATIONS

This application is a National Stage application under 35 U.S.C. § 371 of International Application No. PCT/GB2017/051914, having an International Filing Date of Jun. 29, 2017, which claims the benefit of EP Application No. 1611547.9 filed Jul. 1, 2016. This disclosures of the prior applications are considered part of (and are incorporated by reference in) the disclosure of their application.

BACKGROUND TO THE INVENTION

The use of cannabinoids in medicine has necessitated finding more effective ways of drug delivery. This is in part due to factors such as, poor aqueous solubility, limited bioavailability, and cannabinoid instability, but the use of cannabinoids at relatively high doses (in daily amounts of up to 2000 mg) and/or in challenging patient groups, e.g. young children, and/or for particular indications, can create additional challenges.

There are currently three commercially available cannabinoid formulations on the market.

Dronabinol (Marinol®) is a synthetic tetrahydrocannabinol (THC) which is delivered orally, in sesame oil as capsules.

Nabilone (Cesamet®) is a synthetic cannabinoid and an analog of THC and is delivered orally in capsules with povidone and corn starch.

Nabiximols (Sativex®) is a natural extract of cannabinoids containing defined amounts of THC and Cannabidiol (CBD) and is delivered as a liquid, by way of an oromucosal spray.

The applicant also provides an oral solution containing CBD (Epidiolex®) on a named patient basis. The CBD is formulated in sesame seed oil and further comprises the sweetener sucralose (600× the sweetness intensity of sucrose), strawberry flavouring and up to 10% v/v ethanol.

Whilst there is no clear FDA guidance for maximum allowable ethanol concentration in prescription medicines, an article (Ethanol in Liquid Preparations Intended for Children, Paediatrics: Official Journal of The American Academy of Paediatrics, 1984: 73:405), recommends that a Blood Alcohol Concentration (BAC) of 0.25 g/L (250 mg/L) should not be exceeded following a single dose of alcohol containing medications.

WO 2015/184127 (Insys) discloses a number of different oral formulations including: an alcohol free formulation in which the cannabinoid is formulated in a mix of polyethylene glycol and propylene glycol, optionally with water, a formulation containing alcohol and a formulation containing lipids. In each of the formulations disclosed, the cannabinoid is a synthetically produced (as opposed to a naturally extracted) cannabidiol.

The specification teaches the inclusion of a number of pharmaceutically acceptable excipients such as, anti-oxidants, sweeteners, enhancers, preservatives, flavouring agents and pH modifiers.

According to European Medicine Agency draft guideline (EMA/CHMP/507988/2013), for 2 to 6 years old children, a theoretical limit for Blood Alcohol Concentration (BAC) following single administration of a formulation containing alcohol is not more than 0.01 g/L (10mg/L) and ethanol intake should be not more than 6 mg/kg/day.

For paediatric products aimed at younger children, it is desirable to have low or no ethanol formulations, preferably dispensed as syrup, as younger children find it difficult to swallow capsules. They also favour sweet, flavoured products, particularly where the taste of cannabinoid requires masking.

A problem with the use of pharmaceutically acceptable sweeteners, and flavouring agents is that they are generally polar in nature, and thus unlike the cannabinoids which are highly lipophilic, they require a polar solvent to dissolve them.

An object of the present invention was to develop a lipid based oral formulation which contained less than 10% (v/v) ethanol, which was palatable, and could be delivered to young children as syrup, in relatively small volumes, typically less than 10 ml.

BRIEF SUMMARY OF THE DISCLOSURE

In accordance with a first aspect of the present invention there is provided a cannabinoid containing oral solution comprising: a cannabinoid, a lipid solvent, a sweetener and ethanol, characterised in that the sweetener is an ultrahigh potency sweetener.

An ultrahigh potency sweetener is defined herein as a sweetener with a sweetness intensity compared to sucrose of greater than 750.

Preferably the ultrahigh potency sweetener has a sweetness intensity compared to sucrose of greater than 1000, more preferably greater than 5000.

In one embodiment of the invention the ultrahigh potency sweetener is (N-[N-(3,3-dimethylbutyl)-L-α-aspartyl]-L-phenylalanine 1-methyl ester) (Neotame).

In a further embodiment the ultrahigh potency sweetener is N-[N-3-(3-hydroxy-4-methoxyphenyl)propyl-α-L-aspartyl]-L-phenylalanine 1-methyl ester) (Advantame).

Preferably the cannabinoid containing oral solution further comprises a flavourant.

Preferably the cannabinoid is selected from: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA). More preferably the cannabinoid is CBD.

It is preferred that the cannabinoid containing oral solution has a cannabinoid present in an amount of from 5 to 40% (w/v), ethanol present in an amount of less than 2% (w/v), ultrahigh potency sweetener present in less than 0.05% (w/v) flavourant, more preferably still less than 0.01% (w/v) flavourant present in an amount of less 0.2% (w/v) and lipid solvent present q.s. to 100%.

More preferably the cannabinoid is CBD, the ultrahigh potency sweetener is Neotame, the flavourant is strawberry flavour and the lipid solvent is sesame oil.

Preferably the cannabinoid containing oral solution is stable in climatic zones I and II for up to 24 months at 25° C. or is stable in climatic zones III and IV for up to 18 months at 30° C.

Surprisingly, the formulations of the invention were stable without the need for the incorporation of stability enhancers such as anti-oxidants or complexing agents.

Preferably the cannabinoid containing oral solution is absent of a stabilizing agent.

More preferably the stabilizing agent which the cannabinoid containing oral solution is absent of is an antioxidant or a chelating agent.

The formulation may be packaged for use in a bottle, oral or enteral syringe, metered dose device or other container used to store or administer liquid oral medications.

In accordance with a second aspect of the present invention there is provided a method of treating a subject comprising administering a cannabinoid containing oral solution.

Preferably the subject is a human.

Preferably the cannabinoid containing oral solution is for use in the treatment of epilepsy and syndromes associated therewith, Dravet Syndrome, Lennox Gastaut Syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumors, neuropathic pain, cannabis use disorder, post-traumatic stress disorder, anxiety, early psychosis, Alzheimer's Disease, and autism.

In accordance with a third aspect of the present invention there is provided a cannabinoid containing oral solution for use in the treatment of a disease or disorder selected from the group consisting of epilepsy and syndromes associated therewith, Dravet Syndrome, Lennox Gastaut Syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumors, neuropathic pain, cannabis use disorder, post-traumatic stress disorder, anxiety, early psychosis, Alzheimer's Disease, and autism.

DETAILED DESCRIPTION

The Applicant initially sought to replace the ethanol in their oral lipid formulation with an alternative pharmaceutically acceptable solvent, such as propylene glycol, polyethylene glycol or glycerin but found their miscibility with sesame oil, across a range of concentrations (0.5-10%) tested, was not satisfactory.

They then looked at substituting the sweetener they used, sucralose, with an alternative pharmaceutically acceptable sweetener, such as, for example, sucrose, aspartame, saccharin, dextrose, mannitol or xylitol without success due to for example, taste profile or physical stability.

When these two approaches failed they, unconventionally, tried ultrahigh potency sweeteners, which whilst approved by the FDA in foods, are not generally considered as sweeteners for use in pharmaceuticals. The two tested, Advantame and Neotame proved surprisingly effective and formulations containing these sweeteners did not require stabilizing with anti-oxidants and chelating agents as is common in cannabinoid containing formulations. The Examples that follow describe the development of the claimed formulations which show good stability.

EXAMPLE 1

Selection of Alternative Sweeteners

Alternative sweeteners to sucralose (comparator) were selected as shown in Table 1 below.

TABLE 1

| Sweetener | Acceptable Daily Intake (mg/kg/day)* | Multiplier of Sweetness Intensity Compared to Table Sugar (Sucrose) |
| --- | --- | --- |
| Sucralose | 5 | 600 x |
| Saccharin | 15 | 200-700 x |
| Saccharin Dihydrate | 15 | 200-700 x |
| Aspartame | 50 | 200 x |
| Neotame | 0.3 | 7,000-13,000 x |
| Advantame | 32.8 | 20,000 x |

*Acceptable daily intake values derived from FDA website: http://www.fda.gov/Food/IngredientsPackagingLabeling/FoodAdditivesIngredients/ucm397725.htm#SummaryTable Batches using these sweeteners were prepared as shown in Table 2 below, with the concentrations of each sweetener being selected based on its relative sweetness compared to sucralose.

TABLE 2

| Ingredients | Batch ET03/049C | Batch ET03/049D | Batch ET03/049A | Batch ET03/049B | Batch ET03/012I |
| --- | --- | --- | --- | --- | --- |
| Saccharin | 0.05% w/v | — | — | — | — |
| Saccharin Dihydrate | — | 0.05% w/v | — | — | — |
| Aspartame | — | — | 0.15% w/v | — | — |
| Neotame | — | — | — | 0.005% w/v | — |
| Advantame | — | — | — | — | 0.0025% w/v |
| Anhydrous Ethanol | 10% v/v | 10% v/v | 10% v/v | 10% v/v | 2% v/v |
| Strawberry Flavour | 0.10% w/v | 0.10% w/v | 0.10% w/v | 0.10% w/v | 0.10% w/v |
| Refined Sesame Oil | q.s. to 100% | q.s. to 100% | q.s. to 100% | q.s. to 100% | q.s. to 100% |

Four of the five formulations were clear solutions with the exception of Aspartame which did not completely solubilise in ethanol.

The Formulations made with Saccharin and Saccharin dihydrate produced an unpleasant taste, and also had a lingering bitter after taste.

On the other hand, the Formulations made with Neotame and Advantame both had a good taste profile, with no bitter after taste.

Therefore Neotame and Advantame were both considered suitable candidates for further development.

EXAMPLE 2

Evaluation of an Advantame Formulation

An experiment (ET03/015) was carried out to determine the lowest ethanol concentration required to solubilise Advantame. Table 3 details the batches made with various ethanol concentrations ranging from 0.5% to 3.0% v/v.

TABLE 3

| Ingredients | Batch ET03/015 A | Batch ET03/015 B | Batch ET03/015 C | Batch ET03/015 D | Batch ET03/015 E | Batch ET03/015 F |
|---|---|---|---|---|---|---|
| Advantame | | | 0.0025% w/v | | | |
| Strawberry Flavour | | | 0.10% w/v | | | |
| Anhydrous Ethanol | 0.5% v/v | 1.0% v/v | 1.5% v/v | 2.0% v/v | 2.5% v/v | 3.0% v/v |
| Refined Sesame Oil | | | q.s. to 100% | | | |

These batches were stored at 25° C./60% RH and 40° C./75% RH for up to 4 weeks and observed for any signs of precipitation. There was no precipitation observed over the period assessed. Therefore it was concluded that Advantame can be used as a sweetener and can be solubilised at ethanol concentration of at least as low as 0.5% v/v. i.e. the concentration of ethanol required in the formulation can be reduced by a factor of 20 compared to a sucralose containing formulation.

EXAMPLE 3

Preparation of Neotame Formulations

In an experiment (ET03/127), various formulations were prepared with different levels of CBD (25 mg/ml, 100 mg/ml and 200 mg/ml), Neotame (0.005 and 0.01% w/v) and ethanol (0.5 to 3.0% v/v).

The objective of the experiment was to determine the physical stability of the formulations with different concentrations of CBD, Neotame and ethanol. Tables 4 to 6 below detail the compositions of the formulations.

TABLE 4

(CBD 25 mg/ml)

| Ingredients | Batch A/25 | Batch B/25 | Batch C/25 | Batch D/25 | Batch E/25 | Batch F/25 | Batch G/25 | Batch H/25 |
|---|---|---|---|---|---|---|---|---|
| Cannabidiol | | | | 2.5% w/v | | | | |
| Neotame | 0.005% w/v | 0.01% w/v | 0.005% w/v | 0.01% w/v | 0.005% w/v | 0.01% w/v | 0.005% w/v | 0.01% w/v |
| Anhydrous Ethanol | 0.5% v/v | 0.5% v/v | 1.0% v/v | 1.0% v/v | 2.0% v/v | 2.0% v/v | 3.0% v/v | 3.0% v/v |
| Flavour | | | | 0.10% w/v | | | | |
| | | | | q.s. to 100% | | | | |

TABLE 5

(CBD 100 mg/ml)

| Ingredients | Batch A/100 | Batch B/100 | Batch C/100 | Batch D/100 | Batch E/100 | Batch F/100 | Batch G/100 | Batch H/100 |
|---|---|---|---|---|---|---|---|---|
| Cannabidiol | | | | 10.0% w/v | | | | |
| Neotame | 0.005% w/v | 0.01% w/v | 0.005% w/v | 0.01% w/v | 0.005% w/v | 0.01% w/v | 0.005% w/v | 0.01% w/v |
| Anhydrous Ethanol | 0.5% v/v | 0.5% v/v | 1.0% v/v | 1.0% v/v | 2.0% v/v | 2.0% v/v | 3.0% v/v | 3.0% v/v |
| Flavour | | | | 0.10% w/v | | | | |
| Refined Sesame Oil | | | | q.s. to 100% | | | | |

TABLE 6

(CBD 200 mg/ml)

| Ingredients | Batch A/200 | Batch B/200 | Batch C/200 | Batch D/200 | Batch E/200 | Batch F/200 | Batch G/200 | Batch H/200 |
|---|---|---|---|---|---|---|---|---|
| Cannabidiol | | | | 20.0% w/v | | | | |
| Neotame | 0.005% w/v | 0.01% w/v | 0.005% w/v | 0.01% w/v | 0.005% w/v | 0.01% w/v | 0.005% w/v | 0.01% w/v |
| Anhydrous Ethanol | 0.5% v/v | 0.5% v/v | 1.0% v/v | 1.0% v/v | 2.0% v/v | 2.0% v/v | 3.0% v/v | 3.0% v/v |
| Flavour | | | | 0.10% w/v | | | | |
| Refined Sesame Oil | | | | q.s. to 100% | | | | |

EXAMPLE 4

Testing of Neotame Formulations for Physical Stability

The 25 mg/ml and 100 mg/ml batches were tested for physical stability by opening the bottles and allowing them to stand for 2 weeks to let the ethanol evaporate. This was done as a worst case in-use scenario where the bottle is repeatedly opened and closed multiple times during use. The batches were monitored for any signs of precipitation and the ethanol content measured. The results are provided in Table 7.

TABLE 7

| Batch | CBD Assay (mg/ml) Initial | Appearance of Solution Initial | Appearance of Solution Day 14 | Ethanol Content (% v/v) Target | Ethanol Content (% v/v) Initial | Ethanol Content (% v/v) Day 14 |
|---|---|---|---|---|---|---|
| A/25 | 24.6 | Clear | Clear | 0.5 | 0.6 | 0.03 |
| B/25 | 24.6 | Clear | Clear | 0.5 | 0.6 | 0.02 |
| C/25 | 24.9 | Clear | Clear | 1.0 | 1.1 | 0.04 |
| D/25 | 24.4 | Clear | Clear | 1.0 | 1.0 | 0.05 |
| E/25 | 24.3 | Clear | Clear | 2.0 | 2.0 | 0.09 |
| F/25 | 24.8 | Clear | Clear | 2.0 | 2.1 | 0.14 |
| G/25 | 24.3 | Clear | Clear | 3.0 | 3.4 | 0.14 |
| H/25 | 24.3 | Clear | Clear | 3.0 | 3.0 | 0.12 |
| A/100 | 98.9 | Clear | Clear | 0.5 | 0.6 | 0.04 |
| B/100 | 99.2 | Clear | Clear | 0.5 | 0.7 | 0.05 |
| C/100 | 100.0 | Clear | Clear | 1.0 | 1.2 | 0.10 |
| D/100 | 100.1 | Clear | Clear | 1.0 | 1.1 | 0.15 |
| E/100 | 100.1 | Clear | Clear | 2.0 | 2.1 | 0.20 |
| F/100 | 97.4 | Clear | Clear | 2.0 | 2.1 | 0.18 |
| G/100 | 99.9 | Clear | Clear | 3.0 | 3.3 | 0.25 |
| H/100 | 100.4 | Clear | Clear | 3.0 | 3.3 | 0.29 |

All 25 mg/ml and 100 mg/ml batches were clear without any signs of precipitation. The ethanol content dropped significantly at day 14 for all batches; however there were no signs of precipitation of Neotame even after the ethanol content had dropped by more than 85% of its initial concentration. This indicates that Neotame can be physically solubilised at concentrations up to 0.01% w/v in ethanol.

As Neotame is freely soluble in ethanol at room temperature only a small quantity of ethanol is required to keep Neotame solubilised in the formulation. Accordingly it was decided to use Neotame in a formulation at 0.008% w/v concentration for optimum sweetness with ethanol at a concentration of 1% v/v (0.79% w/v).

EXAMPLE 5

Long Term Stability Testing

100mg/ml and 200mg/ml formulations were made up as per Table 8 below>

TABLE 8

| Component | Function | Reference to Quality standard | CBD 100 mg/ml oral solution | CBD 200 mg/ml oral solution |
|---|---|---|---|---|
| Cannabidiol | Active | In-house | 10.0% w/v | 20.0% w/v |
| Anhydrous Ethanol | Sweetener solubilizer | Ph Eur & USP/NF | 0.79% w/v[†] | 0.79% w/v[†] |
| Neotame | Sweetener | USP/NF | 0.008% w/v | 0.008% w/v |
| Strawberry Flavour | Flavour | In-house | 0.10% w/v | 0.10% w/v |
| Refined Sesame Oil | Solubilizer | Ph Eur & USP/NF | q.s. to 100% | q.s. to 100% |

Note:
[†]0.79% w/v is equivalent to 1% v/v of anhydrous ethanol

The method of manufacture comprised solubilising the CBD in sesame oil. The sweetener and flavour were mixed in ethanol and the ethanolic phase was then mixed with the sesame oil phase containing dissolved CBD.

The long term stability testing was according to ICH guideline (http://www.ich.org/fileadmin/Public_Web_Site/ICH_Products/Guidelines/Quality/Q1A_R2/Step4/Q1A_R2 Guideline.pdf) with different CBD strengths as detailed in Table 9 below.

TABLE 9

| Study Reference | Description | Ingredients | Composition | Storage Conditions |
|---|---|---|---|---|
| DSP-15-10-02 | CBD 100 mg/ml oral solution | CBD | 10.0% w/v | 25° C./60% RH |
| | | Anhydrous Ethanol | 0.79% w/v | 30° C./65% RH |
| | | Neotame | 0.008% w/v | 40° C./75% RH |
| | | Strawberry Flavour | 0.10% w/v | |
| | | Refined Sesame Oil | q.s. to 100% | |

TABLE 9-continued

| Study Reference | Description | Ingredients | Composition | Storage Conditions |
|---|---|---|---|---|
| | CBD 200 mg/ml oral solution | CBD<br>Anhydrous Ethanol<br>Neotame<br>Strawberry Flavour<br>Refined Sesame Oil | 20.0% w/v<br>0.79% w/v<br>0.008% w/v<br>0.10% w/v<br>q.s. to 100% | 25° C./60% RH<br>30° C./65% RH<br>40° C./75% RH |

The tests shown in Table 10 below were used to determine the stability of the formulations.

TABLE 10

| Test | Test method |
|---|---|
| Appearance of Solution | Visual check |
| CBD Content | Ultra-Performance Liquid Chromatography (UPLC) |
| Degradants: | |
| CBE I | |
| CBE II | |
| OH-CBD | |
| Total Degradants | |
| Microbial: | Pharmacopoeial |
| TAMC | |
| TYMC | |
| E. coli | |

The results from illustrated in Tables 11 to 15 for the 100mg/ml CBD formulation and 16 to 20 for the 200 mg/ml CBD formulation.

TABLE 11

Stability data for CBD 100 mg/ml Oral Solution Batch ET04/126-B 25° C. ± 2° C./60% RH ± 5% RH, Vertical

| Test | Specification | Time-point (months) | | | |
|---|---|---|---|---|---|
| | | 0 | 2 | 3 | 6 |
| Appearance of Solution | A clear, colorless to yellow solution | A clear solution free from visible particulates | A clear solution free from visible particulates | A clear solution free from visible particulates | A clear solution free from visible particulates |
| CBD Content | 90.0-110.0 mg/ml (90.0-110.0% LC) | 99.5 mg/ml (99.5%) | 101.3 mg/ml (101.3%) | 99.9 mg/ml (99.9%) | 98.9 mg/ml (98.9%) |
| Degradants | | | | | |
| CBE I | NMT 0.2% | ND | ND | ND | ND |
| CBE II | NMT 0.2% | ND | ND | ND | ND |
| OH-CBD | NMT 0.2% | 0.03% | ND | 0.02% | 0.05% |
| Total Degradants | NMT 1.0% | 0.03% | ND | 0.02% | 0.05% |
| Microbial: | | | | | |
| TAMC | NMT 10³ cfu/g | Complies with pharmacopoeial requirements | Complies with pharmacopoeial requirements | Complies with pharmacopoeial requirements | Complies with pharmacopoeial requirements |
| TYMC | NMT 10² cfu/g | | | | |
| E. coli | Absent in 1 g | | | | |

ND = Not Detected

TABLE 12

Stability data for CBD 100 mg/ml Oral Solution Batch ET04/126-B 30° C. ± 2° C./65% RH ± 5% RH, Vertical

| Test | Specification | Time-point (months) | | | |
|---|---|---|---|---|---|
| | | 0 | 2 | 3 | 6 |
| Appearance of Solution | A clear, colorless to yellow solution | A clear solution free from visible particulates | A clear solution free from visible particulates | A clear solution free from visible particulates | A clear solution free from visible particulates |
| CBD Content | 90.0-110.0 mg/ml (90.0-110.0% LC) | 99.5 mg/ml (99.5%) | 100.8 mg/ml (100.8%) | 99.1 mg/ml (99.1%) | 99.0 mg/ml (99.0%) |

TABLE 12-continued

Stability data for CBD 100 mg/ml Oral Solution Batch ET04/126-B 30° C. ± 2° C./65% RH ± 5% RH, Vertical

| | | Time-point (months) | | | |
|---|---|---|---|---|---|
| Test | Specification | 0 | 2 | 3 | 6 |
| Degradants: | | | | | |
| CBE I | NMT 0.2% | ND | ND | ND | ND |
| CBE II | NMT 0.2% | ND | ND | ND | ND |
| OH-CBD | NMT 0.2% | 0.03% | ND | 0.02% | 0.05% |
| Total Degradants | NMT 1.0% | 0.03% | ND | 0.02% | 0.05% |
| Microbial: | | | | | |
| TAMC | NMT $10^3$ cfu/g | Complies with pharmacopoeial requirements | Complies with pharmacopoeial requirements | Complies with pharmacopoeial requirements | Complies with pharmacopoeial requirements |
| TYMC | NMT $10^2$ cfu/g | | | | |
| E. coli | Absent in 1 g | | | | |

ND = Not Detected

TABLE 13

Stability data for CBD 100 mg/ml Oral Solution Batch ET04/126-B 40° C. ± 2° C./75% RH ± 5% RH, Vertical

| | | Time-point (months) | | |
|---|---|---|---|---|
| Test | Specification | 0 | 2 | 6 |
| Appearance of Solution | A clear, colorless to yellow solution | A clear solution free from visible particulates | A clear solution free from visible particulates | A clear solution free from visible particulates |
| CBD Content | 90.0-110.0 mg/ml (90.0-110.0% LC) | 99.5 mg/ml (99.5%) | 100.8 mg/ml (100.8%) | 98.8 mg/ml (98.8%) |
| Degradants | | | | |
| CBE I | NMT 0.2% | ND | ND | 0.05% |
| CBE II | NMT 0.2% | ND | ND | ND |
| OH-CBD | NMT 0.2% | 0.03% | ND | 0.06% |
| Total Degradants | NMT 1.0% | 0.03% | ND | 0.11% |
| Microbial: | | | | |
| TAMC | NMT $10^3$ cfu/g | Complies with pharmacopoeial requirements | Complies with pharmacopoeial requirements | Complies with pharmacopoeial requirements |
| TYMC | NMT $10^2$ cfu/g | | | |
| E. coli | Absent in 1 g | | | |

ND = Not Detected

TABLE 14

Stability data for CBD 100 mg/ml Oral Solution Batch ET04/126-B In-Use 25° C. ± 2° C./60% RH ± 5% RH, Vertical

| Test | Specification | Time-point (Initial) 8 weeks |
|---|---|---|
| Appearance of Solution | A clear, colorless to yellow solution | A clear solution free from visible particulates |
| CBD Content | 90.0-110.0 mg/ml (90.0-110.0% LC) | 100.3 mg/ml (100.3%) |
| Degradants: | | |
| CBE I | NMT 0.2% | ND |
| CBE II | NMT 0.2% | ND |
| OH-CBD | NMT 0.2% | ND |
| Total | NMT 1.0% | ND |
| Microbial: | | |
| TAMC | NMT $10^3$ cfu/g | Complies with pharmacopoeial requirements |
| TYMC | NMT $10^2$ cfu/g | |
| E. coli | Absent in 1 g | |

ND = Not Detected

TABLE 15

Stability data for CBD 100 mg/ml Oral Solution Batch ET04/126-B In-Use 30° C. ± 2° C./65% RH ± 5% RH, Vertical

| Test | Specification | Time-point (Initial) 8 weeks |
|---|---|---|
| Appearance of Solution | A clear, colorless to yellow solution | A clear solution free from visible particulates |
| CBD Content | 90.0-110.0 mg/ml (90.0-110.0% LC) | 99.7 mg/ml (99.7%) |
| Degradants: | | |
| CBE I | NMT 0.2% | ND |
| CBE II | NMT 0.2% | ND |
| OH-CBD | NMT 0.2% | ND |
| Total | NMT 1.0% | ND |
| Degradants Microbial: | | |
| TAMC | NMT $10^3$ cfu/g | Complies with pharmacopoeial requirements |
| TYMC | NMT $10^2$ cfu/g | |
| E. coli | Absent in 1 g | |

ND = Not Detected

TABLE 16

Stability data for CBD 200 mg/ml Oral Solution Batch ET04/126-C 25° C. ± 2° C./60% RH ± 5% RH, Vertical

| Test | Specification | 0 | 2 | 3 | 6 |
|---|---|---|---|---|---|
| Appearance of Solution | A clear, colorless to yellow solution | A clear solution free from visible particulates | A clear solution free from visible particulates | A clear solution free from visible particulates | A clear solution free from visible particulates |
| CBD Content | 180.0-220.0 mg/ml (90.0-110.0% LC) | 199.5 mg/ml (99.7%) | 202.3 mg/ml (101.2%) | 198.2 mg/ml (99.1%) | 198.3 mg/ml (99.1%) |
| Degradants: | | | | | |
| CBE I | NMT 0.2% | ND | ND | ND | ND |
| CBE II | NMT 0.2% | ND | ND | ND | ND |
| OH-CBD | NMT 0.2% | 0.04% | ND | 0.02% | 0.04% |
| Total Degradants | NMT 1.0% | 0.04% | ND | 0.02% | 0.04% |
| Microbial: | | | | | |
| TAMC | NMT $10^3$ cfu/g | Complies with pharmacopoeial requirements | Complies with pharmacopoeial requirements | Complies with pharmacopoeial requirements | Complies with pharmacopoeial requirements |
| TYMC | NMT $10^2$ cfu/g | | | | |
| E. coli | Absent in 1 g | | | | |

ND = Not Detected

TABLE 17

Stability data for CBD 200 mg/ml Oral Solution Batch ET04/126-C 30° C. ± 2° C./65% RH ± 5% RH, Vertical

| Test | Specification | 0 | 2 | 3 | 6 |
|---|---|---|---|---|---|
| Appearance of Solution | A clear, colorless to yellow solution | A clear solution free from visible particulates | A clear solution free from visible particulates | A clear solution free from visible particulates | A clear solution free from visible particulates |
| CBD Content | 180.0-220.0 mg/ml (90.0-110.0% LC) | 199.5 mg/ml (99.7%) | 201.8 mg/ml (100.9%) | 199.4 mg/ml (99.7%) | 198.0 mg/ml (99.0%) |
| Degradants: | | | | | |
| CBE I | NMT 0.2% | ND | ND | ND | ND |
| CBE II | NMT 0.2% | ND | ND | ND | ND |
| OH-CBD | NMT 0.2% | 0.04% | ND | 0.01% | 0.04% |
| Total | NMT 1.0% | 0.04% | ND | 0.01% | 0.04% |

TABLE 17-continued

Stability data for CBD 200 mg/ml Oral Solution Batch ET04/126-C 30° C. ± 2° C./65% RH ± 5% RH, Vertical

| | | Time-point (months) | | | |
|---|---|---|---|---|---|
| Test | Specification | 0 | 2 | 3 | 6 |
| Degradants Microbial: | | | | | |
| TAMC | NMT $10^3$ cfu/g | Complies with pharmacopoeial requirements | Complies with pharmacopoeial requirements | Complies with pharmacopoeial requirements | Complies with pharmacopoeial requirements |
| TYMC | NMT $10^2$ cfu/g | | | | |
| E. coli | Absent in 1 g | | | | |

ND = Not Detected

TABLE 18

Stability data for CBD 200 mg/ml Oral Solution Batch ET04/126-C 40° C. ± 2° C./75% RH ± 5% RH, Vertical

| | | Time-point (months) | | |
|---|---|---|---|---|
| Test | Specification | 0 | 2 | 6 |
| Appearance of Solution | A clear, colorless to yellow solution | A clear solution free from visible particulates | A clear solution free from visible particulates | A clear solution free from visible particulates |
| CBD Content | 180.0-220.0 mg/ml (90.0-110.0% LC) | 199.5 mg/ml (99.7%) | 202.3 mg/ml (101.2%) | 197.9 mg/ml (99.0%) |
| Degradants: | | | | |
| CBE I | NMT 0.2% | ND | ND | 0.04% |
| CBE II | NMT 0.2% | ND | ND | ND |
| OH-CBD | NMT 0.2% | 0.04% | ND | 0.05% |
| Total Degradants | NMT 1.0% | 0.04% | ND | 0.09% |
| Microbial: | | | | |
| TAMC | NMT $10^3$ cfu/g | Complies with pharmacopoeial requirements | Complies with pharmacopoeial requirements | Complies with pharmacopoeial requirements |
| TYMC | NMT $10^2$ cfu/g | | | |
| E. coli | Absent in 1 g | | | |

ND = Not Detected

TABLE 19

Stability data for CBD 200 mg/ml Oral Solution Batch ET04/126-C In-Use 25° C. ± 2° C./60% RH ± 5% RH, Vertical

| Test | Specification | Time-point (Initial) 8 weeks |
|---|---|---|
| Appearance of Solution | A clear, colorless to yellow solution | A clear solution free from visible particulates |
| CBD Content | 180.0-220.0 mg/ml (90.0-110.0% LC) | 198.7 mg/ml (99.4%) |
| Degradants: | | |
| CBE I | NMT 0.2% | ND |
| CBE II | NMT 0.2% | ND |
| OH-CBD | NMT 0.2% | ND |
| Total Degradants | NMT 1.0% | ND |
| Microbial: | | |
| TAMC | NMT $10^3$ cfu/g | Complies with pharmacopoeial requirements |
| TYMC | NMT $10^2$ cfu/g | |
| E. coli | Absent in 1 g | |

ND = Not Detected

TABLE 20

Stability data for CBD 200 mg/ml Oral Solution (Re-formulation) Batch ET04/126-C In-Use 30° C. ± 2° C./65% RH ± 5% RH, Vertical

| Test | Specification | Time-point (initial) 8 weeks |
|---|---|---|
| Appearance of Solution | A clear, colorless to yellow solution | A clear solution free from visible particulates |
| CBD Content | 180.0-220.0 mg/ml (90.0-110.0% LC) | 199.2 mg/ml (99.6%) |
| Degradants: | | |
| CBE I | NMT 0.2% | ND |
| CBE II | NMT 0.2% | ND |
| OH-CBD | NMT 0.2% | ND |
| Total Degradants | NMT 1.0% | ND |
| Microbial: | | |
| TAMC | NMT $10^3$ cfu/g | Complies with pharmacopoeial requirements |
| TYMC | NMT $10^2$ cfu/g | |
| E. coli | Absent in 1 g | |

ND = Not Detected

Conclusions

From these data it can be concluded that both the 100 mg/ml and the 200 mg/ml CBD containing formulations are stable up to 6 months under both normal and accelerated conditions and the inference is that the formulations will support shelf life of at least:

Climatic Zone I and II—24 months, Store below 25° C.
Climatic Zone III and IV—18 month, Store below 30° C.

EXAMPLE 6

Safety Levels

The Neotame containing, formulations of Table 8 illustrate the fact that both levels of Neotame and ethanol are well below recommended guidelines when the CBD is used at a dose of 20 mg/kg.

Neotame.

Assuming a maximum CBD dose of 20 mg/kg/day, the maximum Neotame dose at 0.008% w/v concentration in the formulation would be 0.016 mg/kg/day with the 100 mg/ml CBD formulation and 0.008 mg/kg/day with the 200 mg/ml CBD formulation. These are well below the acceptable daily intake limits for Neotame of 0.3 mg/kg/day, as per the FDA guidelines for food.

Ethanol

According to European Medicine Agency draft guideline (EMA/CHMP/507988/2013), for 2-6 years old children a theoretical limit for Blood Alcohol Concentration (BAC) following a single administration of formulation containing alcohol is not more than 0.01 g/L (10 mg/L), and ethanol intake should be exceed 6 mg/kg/day.

The theoretical BAC and maximum ethanol intake for proposed formulations containing 1% v/v ethanol, assuming a max CBD dose of 20 mg/kg/day are detailed in Table 21 below.

TABLE 21

| Formulation | Theoretical BAC | Ethanol intake |
|---|---|---|
| CBD 100 mg/ml solution | 0.001 g/L | 1.58 mg/kg/day |
| CBD 200 mg/ml solution | 0.0005 g/L | 0.79 mg/kg/day |

It is evident that they are well below the specified limits.

The invention claimed is:

1. A pharmaceutical formulation for oral administration comprising:
   cannabidiol (CBD);
   a lipid solvent;
   an ultrahigh potency sweetener; and
   ethanol, wherein ethanol has a concentration of less than about 3% v/v.

2. The pharmaceutical formulation of claim 1, wherein the ultrahigh potency sweetener has a sweetness intensity that is 1000x greater than sucrose.

3. The pharmaceutical formulation of claim 1, wherein the ultrahigh potency sweetener has a sweetness intensity that is 5000x greater than sucrose.

4. The pharmaceutical formulation of claim 1, wherein the ultrahigh potency sweetener is (N-[N-(3,3-dimethylbutyl)-L-α-aspartyl]-L-phenylalanine 1- methyl ester) (Neotame).

5. The pharmaceutical formulation of claim 1, wherein the ultrahigh potency sweetener is N-[n-3-(3-hydroxy-4methoxyphenyl)propyl-α-L-aspartyl] -L-phenylalanine 1-methyl ester) (Advantame).

6. The pharmaceutical formulation of claim 1, further comprising a flavorant.

7. The pharmaceutical formulation of claim 1, wherein the CBD is present in an amount of from 5 to 40% (w/v), ethanol is present in an amount of less than 2% (v/v), ultrahigh potency sweetener is present in less than 0.05% (w/v), flavorant is present in an amount of less 0.2% (w/v) and lipid solvent is q.s. to 100%.

8. The pharmaceutical formulation of claim 7, wherein the ultrahigh potency sweetener is Neotame, the flavorant is strawberry flavor and the lipid solvent is sesame oil.

9. The pharmaceutical formulation of claim 1, wherein the formulation is stable in climatic zones I and II for up to 24 months at 25° C.

10. The pharmaceutical formulation of claim 1, wherein the formulation is stable in climatic zones III and IV for up to 18 months at 30° C.

11. The pharmaceutical formulation of claim 1, wherein the solution lacks a stabilizing agent.

12. The pharmaceutical formulation of claim 8, wherein the formulation is stable in climatic zones I and II for up to 24 months at 25° C.

13. The pharmaceutical formulation of claim 8, wherein the formulation is stable in climatic zones III and IV for up to 18 months at 30° C.

14. The pharmaceutical formulation of claim 8, wherein the solution lacks a stabilizing agent.

15. The pharmaceutical formulation of claim 1, the ultrahigh potency sweetener is Neotame, and the lipid solvent is sesame oil.

16. The pharmaceutical formulation of claim 1, wherein the concentration of ethanol is less than about 2% (v/v).

17. The pharmaceutical formulation of claim 1, wherein the concentration of ethanol ranges from about 0.5% (v/v) to 3% (v/v).

18. The pharmaceutical formulation of claim 1, wherein the lipid solvent is sesame oil.

19. The pharmaceutical formulation of claim 1, wherein:
   the CBD is present in an amount ranging from 5 to 40% (w/v);
   the ethanol is present in an amount ranging from 0.5% (v/v) to 2% (v/v);
   the ultrahigh potency sweetener is present in an amount ranging from 0.01% (w/v) to 0.0025% about;
   flavorant is present in an amount of less 0.2% (w/v); and
   sesame oil is q.s. to 100%.

20. The pharmaceutical formulation of claim 1, wherein the CBD is present in an extract.

* * * * *

UNITED STATES PATENT AND TRADEMARK OFFICE
CERTIFICATE OF CORRECTION

| | |
|---|---|
| PATENT NO. | : 11,291,631 B2 |
| APPLICATION NO. | : 16/314569 |
| DATED | : April 5, 2022 |
| INVENTOR(S) | : Shah |

It is certified that error appears in the above-identified patent and that said Letters Patent is hereby corrected as shown below:

In the Claims

At Claim 19, Column 18, Line 53, replace:
"0.0025% about;"
With:
--0.0025%;--

Signed and Sealed this
First Day of November, 2022

Katherine Kelly Vidal
*Director of the United States Patent and Trademark Office*